United States Patent [19]

Kirmann

[11] Patent Number: Plant 6,027

[45] Date of Patent: Sep. 29, 1987

[54] GERANIUM PLANT NAMED MARY

[75] Inventor: Wolfgang Kirmann, Langenzersdorf, Austria

[73] Assignee: Mirko Vavra, Bisamberg, Austria

[21] Appl. No.: 811,167

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Mary having pure white flower color, the petals being variegated with pink; floriferous, strong growth habit; medium green foliage; good bud production at night temperatures up to 16° C., thus providing a long and continuous flowering period; medium early flowering; and ease of propagation and good rooting habit.

2 Drawing Figures

The present invention comprises a new and distinct cultivar of geranium, botanically known as *Pelargonium domesticum,* and hereinafter referred to by the cultivar name Mary.

Mary is a product of a planned breeding program which had the objective of creating new geranium cultivars having white flower color, medium green foliage, long lasting flowers, good flower production and normal growth habit.

Mary was originated from a hybridization made by applicant in a controlled breeding program in Bisamberg, Austria in 1976. The female parent was a cultivar designated seedling 01, characterized by its compact growth habit and white flower color with lilac markings. The male parent of Mary was Destiny, a cultivar having pure white flower color but sensitive foliage and an unbalanced growth habit.

Mary was discovered and selected as one flowering plant within the progeny of the stated cross by applicant on Apr. 24, 1977 in a controlled environment in Bisamberg, Austria.

The first act of asexual reproduction of Mary was accomplished when vegetative cuttings were taken from the initial selection on Aug. 31, 1977 in a controlled environment in Bisamberg, Austria by a technician working under formulations established and supervised by Wolfgang Kirmann. Horticultural examination of selected units initiated in the spring of 1978 has demonstrated that the combination of characteristics as herein disclosed for Mary are firmly fixed and are retained through successive generations of asexual reproduction.

Mary has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Mary, which in combination distinguish this geranium as a new and distinct cultivar.

1. Pure white flower color, with pink variegation.
2. Propagates well with very good rooting habit.
3. Excellent bud production and very floriferous.

4. Medium early spring flowering response.
5. Medium green foliage.
6. Strong growth habit.
7. Buds are produced under normal greenhouse conditions (5000 Lux for 16 hours per day) at 14°–16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.
8. Mary is unique with regard to the combined features of compactness, continuous flowering, floriferous habit, and pure white flower color.

Of the many commercial cultivars known to the present inventor, the most similar in comparison to Mary is Destiny, an unpatented but commercial cultivar. In comparison to Destiny, Mary has a more compact, uniform, upright growth habit and longer lasting flowers.

The accompanying photographic drawings show typical flower and foliage characteristics of Mary, with colors being as true as possible with illustrations of this type.

Sheet 1 is a perspective view of a potted plant of Mary.

Sheet 2 is a black and white print showing the upper surface of immature and mature plants of Mary.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

Classification:

*Botanical.—Pelargonium domesticum.*

*Commercial.*—Commonly referred to as a "Martha Washington" geranium, and having the cultivar name Mary.

INFLORESCENCE

A. Umbel:

*Average diameter.*—Relatively large, 120–125 mm.

*Peduncle length.*—Normal.

*Pedicel length.*—Normal.

B. Corolla:

*Average diameter.*—80–85 mm; total inflorescence diameter is within the foliage.

*Form.*—5 or more petals.

*Color (general tonality from a distance of three meters).*—White with deep pink variegation on upper petals.

*Color (upper surface).*—White, upper petals variegated with 63A.

C. Bud:

*Shape.*—Elongated.

*Color.*—White.

D. Reproductive organs:

*Androecium.*—Reddish-yellow.

*Gynoecium.*—Normal.

E. Spring flowering response period: Medium early.

F. Durability: Good.

PLANT

A. Foliage:

*Form.*—Zygomorphic with a nectar spur.

*Margin.*—Crenate.

*Color (upper surface).*—Medium green, 137A.

*Tolerance of Botrytis and soil fungi.*—Good.

B. General appearance and form:

*Internode length.*—Medium.

*Branching pattern.*—Good.

*Height.*—Medium.

I claim:

1. A new and distinct cultivar of geranium named Mary, as described and illustrated, and particularly characterized by its pure white flower color, with the petals being variegated with pink; floriferous, strong growth habit; good bud production at night temperatures up to 16° C., thus providing a long and continuous flowering period; medium green foliage; medium early flowering; and ease of propagation and good rooting habit.

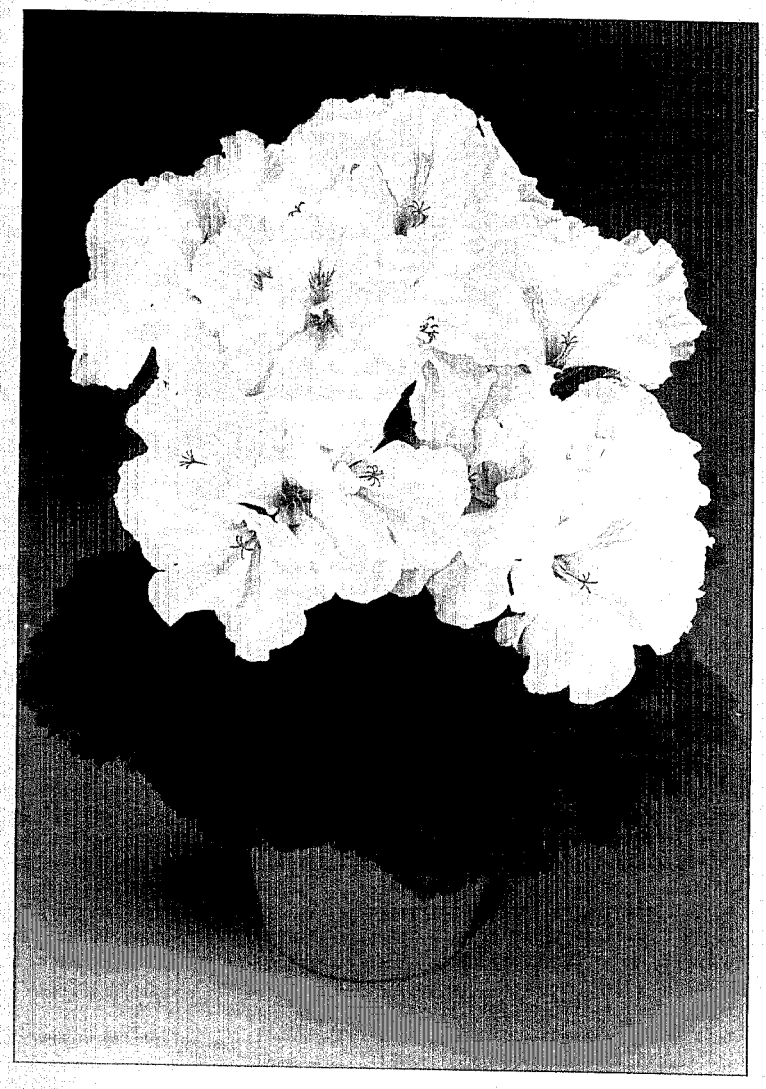

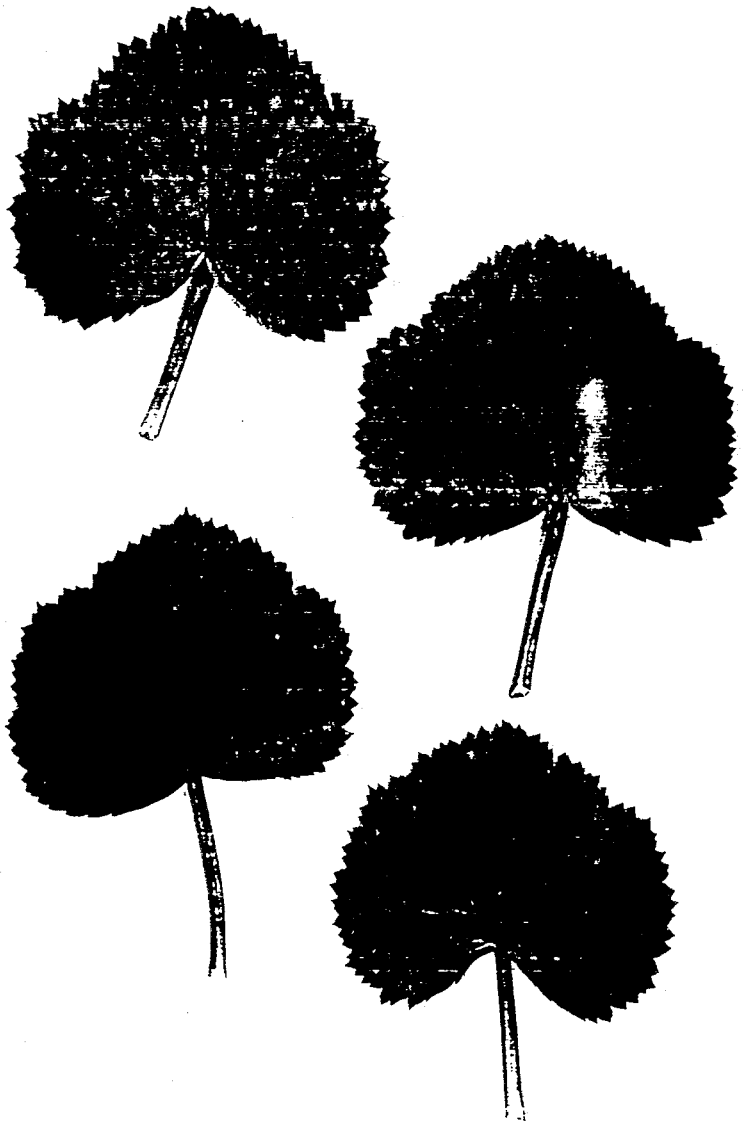

* * * * *